(12) United States Patent
Willliams

(10) Patent No.: US 7,364,559 B2
(45) Date of Patent: Apr. 29, 2008

(54) CO-DYNAMIC ADJUSTABLE ORTHOTIC APPLIANCE FOR CARPAL TUNNEL SYNDROME

(76) Inventor: George Roger Willliams, 3024 SE. 40th St., Edmond, OK (US) 73013

( * ) Notice: Subject to any disclaimer, the term of this patent is extended or adjusted under 35 U.S.C. 154(b) by 0 days.

(21) Appl. No.: 10/352,837

(22) Filed: Jan. 28, 2003

(65) Prior Publication Data

US 2003/0144692 A1    Jul. 31, 2003

(51) Int. Cl.
*A61F 5/00* (2006.01)
(52) U.S. Cl. ...................................... 602/21
(58) Field of Classification Search ........... 602/6, 602/23, 5, 19–22, 60–64; 128/878–879; 2/16, 20; *A61F 3/00*
See application file for complete search history.

(56) References Cited

U.S. PATENT DOCUMENTS

| | | | |
|---|---|---|---|
| 1,174,675 A * | 3/1916 | Cady et al. ................. | 602/21 |
| 1,313,344 A * | 8/1919 | Smart ....................... | 602/6 |
| 1,867,258 A * | 7/1932 | Fruehauf .................... | 602/22 |
| 2,703,082 A * | 3/1955 | Emert ........................ | 128/881 |
| 3,938,509 A * | 2/1976 | Barber ....................... | 602/21 |
| 4,677,971 A | 7/1987 | Lindemann | |
| 4,768,502 A * | 9/1988 | Lee ........................... | 602/6 |
| 4,928,677 A * | 5/1990 | Barber ........................ | 602/21 |
| 5,409,451 A * | 4/1995 | Daneman ..................... | 602/21 |
| 5,413,553 A | 5/1995 | Downes | |
| 5,649,900 A | 7/1997 | Kline | |
| 5,653,680 A | 8/1997 | Cruz | |
| 5,695,453 A * | 12/1997 | Neal .......................... | 602/6 |
| 5,713,836 A * | 2/1998 | O'keefe ...................... | 602/5 |
| 5,730,711 A | 3/1998 | Kendall et al. | |
| 5,746,707 A | 5/1998 | Eck | |
| 5,759,166 A * | 6/1998 | Nelson et al. ............... | 602/21 |
| 5,810,753 A * | 9/1998 | Eberbach .................... | 602/21 |
| 5,868,692 A * | 2/1999 | Michniewicz ............... | 602/21 |
| 5,919,151 A | 7/1999 | Gustafson | |
| 5,921,949 A | 7/1999 | Dray | |
| 5,980,476 A | 11/1999 | Wiederrich | |
| 6,048,325 A | 4/2000 | Kendall et al. | |
| 6,106,492 A | 8/2000 | Darcey | |
| 6,146,347 A | 11/2000 | Porrata | |
| 6,200,286 B1 | 3/2001 | Zamani | |
| 6,213,969 B1 | 4/2001 | MacMorran et al. | |
| 6,217,536 B1 | 4/2001 | Gustafson | |

(Continued)

*Primary Examiner*—Patricia Bianco
*Assistant Examiner*—Huong Q. Pham
(74) *Attorney, Agent, or Firm*—James F. Harvey, III; Doerner Saunders Daniel & Anderson, LLP

(57) ABSTRACT

The present invention provides an orthotic appliance for the carpus of a human hand for the treatment of carpal tunnel syndrome using co-dynamic, rather than traditional static or dynamic, techniques. The appliance may apply a 2 pound dorsally directed force about the region of the pisiform bone in the neutral carpal position of a human hand upon co-contraction of the hand and up to 8 pounds dorsally directed during arc of motion in carpal flexion, as the wrist and hand is encouraged to actively move in all planes of motion without negatively affecting the normal activities of daily living. The appliance may comprise a biasing structure for applying the dorsally directed force and a base structure for maintaining the biasing structure in its proper configuration during normal hand motion.

20 Claims, 8 Drawing Sheets

U.S. PATENT DOCUMENTS 6,238,358 B1 * 5/2001 Philot et al. .................. 602/5
6,293,919 B1 9/2001 Manente
6,315,748 B1 11/2001 Morgan, Jr.
6,723,061 B2 * 4/2004 Williams .................... 602/21

* cited by examiner

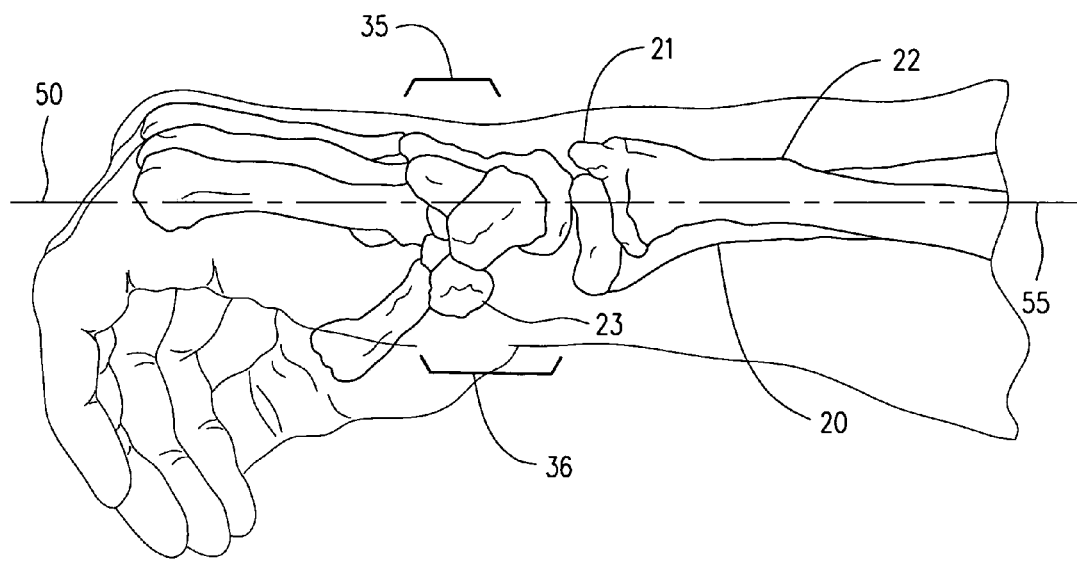
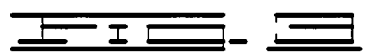
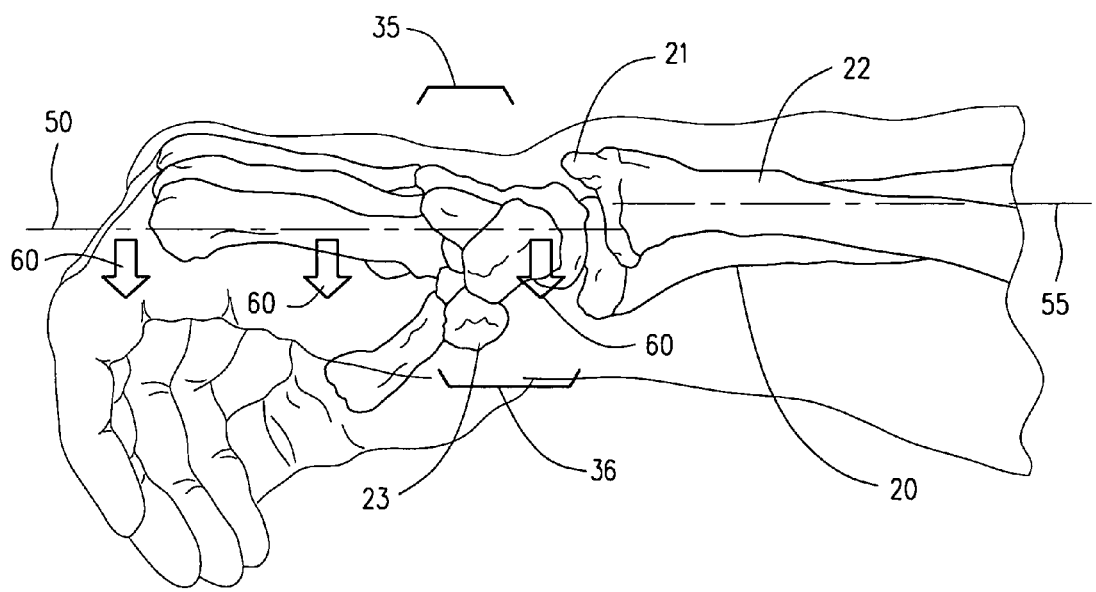
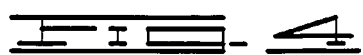

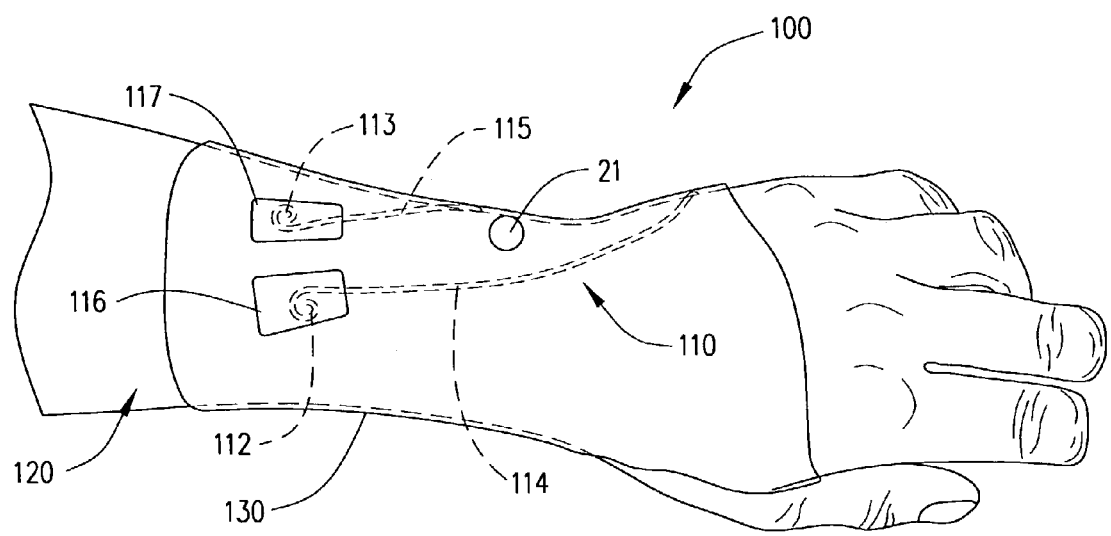
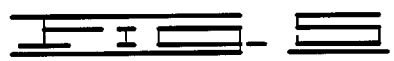
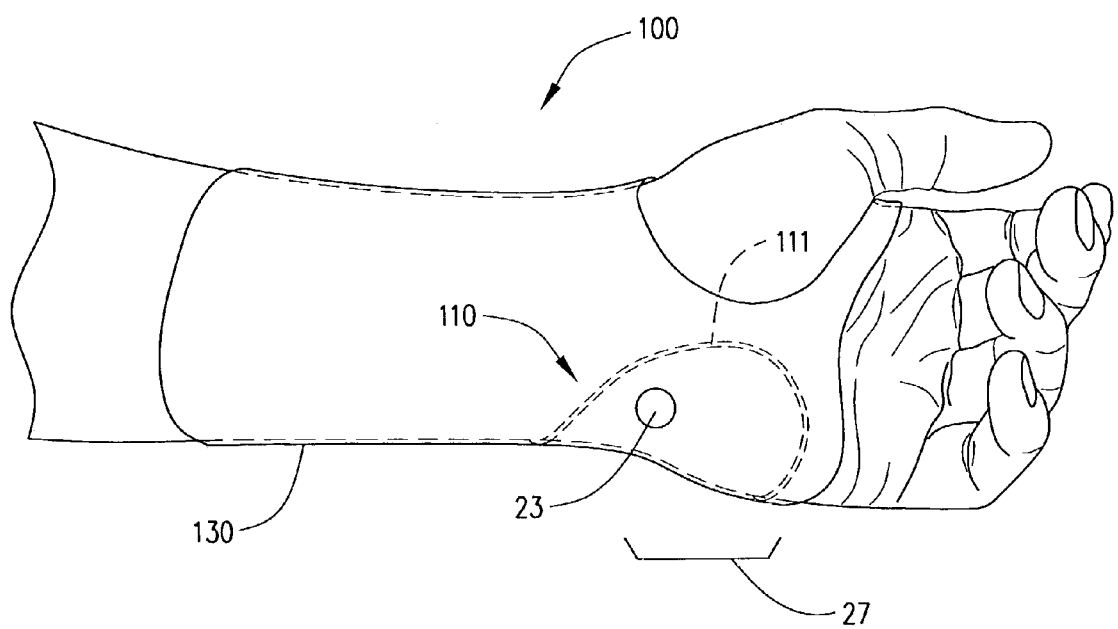

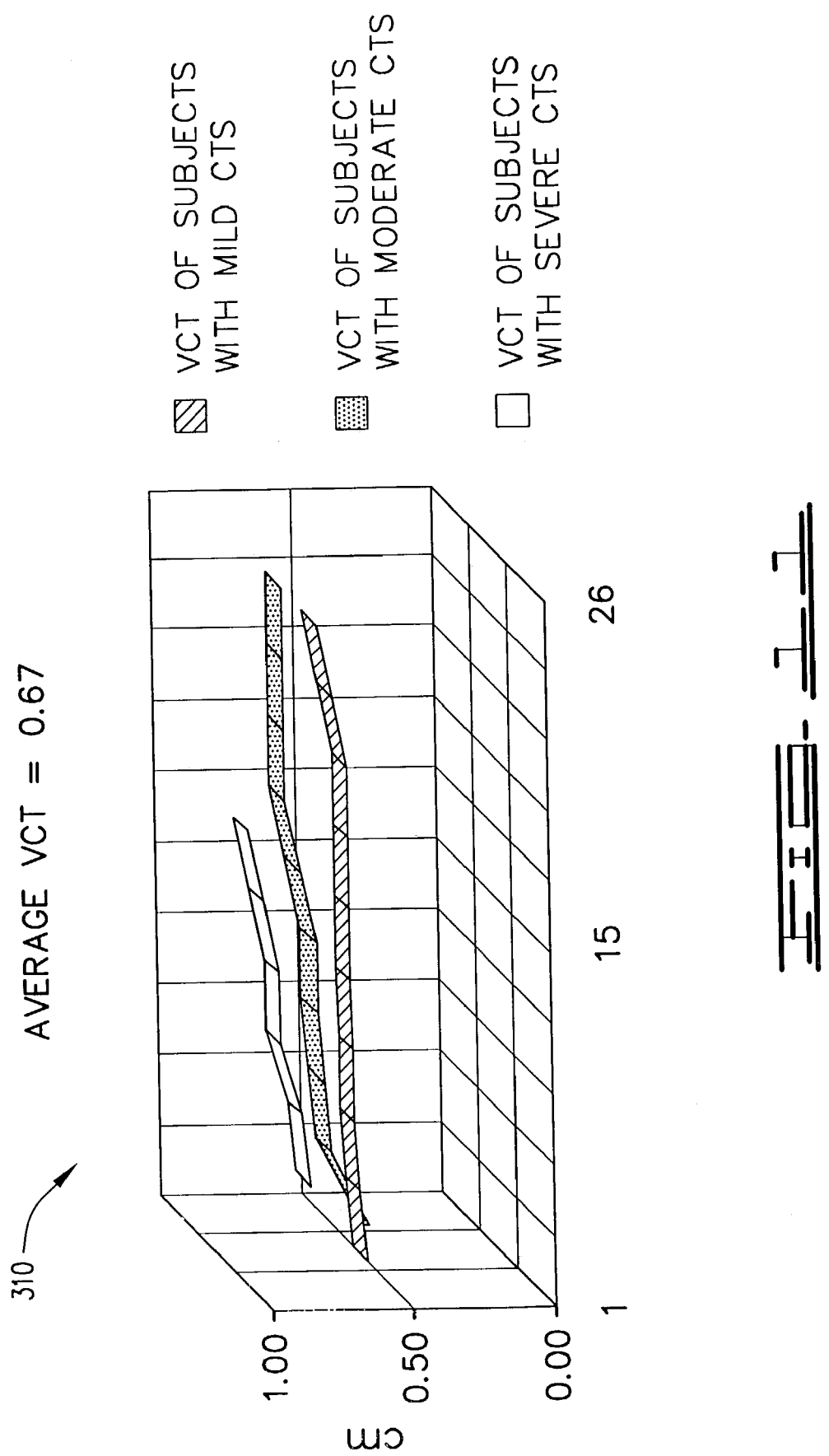

CO-DYNAMIC ADJUSTABLE ORTHOTIC APPLIANCE FOR CARPAL TUNNEL SYNDROME

TECHNICAL FIELD OF THE INVENTION

The present invention relates generally to the field of orthotics and splints for the carpus of a human hand, and more particularly to an orthotic for the treatment of carpal tunnel syndrome using dynamic and co-dynamic, rather than static, techniques.

BACKGROUND OF THE INVENTION

Carpal Tunnel Syndrome ("CTS") is a condition resulting from the compression of the median nerve that travels through an area in carpus of the hand between the carpal bones and a ligament known as the flexor retinaculum. The compression results in numbness, tingling, weakness in the grip, and pain. CTS produces pain and paresthesia in the arm and often-referred symptoms to the shoulders and neck.

There are many theories as to the causes of CTS. Some believe that it results from irritation of bursa, tendon sheaths, and nerve causing tunnel swelling from repetitive motion. Others attribute CTS to carpal fractures or arthritic joint changes. Still other schools of thought attribute CTS to systemic disease, mechanical stress, or traumatic dislocation. The compression theory that is widely accepted holds that irritated and inflamed tissue resulting from these events within the carpal tunnel compresses the median nerve within the confined space formed by the flexor retinaculum and the carpal bones. Discussion will later allude to the order of events rather than questioning the different perspective. The vast number of cases of CTS is generally believed to be due to repetitive motion.

Traditionally, approaches to treating CTS may be classified as being either conservative or surgical. Surgical treatment of CTS may include open resection of the flexor retinaculum, arthroscopy, and other invasive procedures. Although the surgery is often used as a first line of treatment especially in workers compensation cases, the treatment is permanent and often not effective in the end. The result of surgery often results in return of some symptoms within five years according to the U.S. Bureau of Labor Statistics and patients may incur a lifetime of dysfunction due to scar pain and weakness.

Conservative treatment may consist of rest; steroid injection; application of heat, ultrasound, or phonophoresis to the carpal area; exercising the hand through squeezing putty or tennis balls; or splinting of the carpal area through either static or dynamic means. Steroid injection is often the drug therapy of choice, but this therapy is limited in the number of times it may be applied, may cause serious complications, and demonstrates poor long term resolution of symptoms. Immobilization of the wrist through static wrist splinting prevents movement in one or more planes of motion. U.S. Pat. No. 6,106,492, issued to Darcy, discloses a carpal tunnel splint with a rigid outer shell that immobilizes the wrist while applying pressure upon the metacarpals. Wrist braces and splints that utilize such immobilization address the conventional thought that repetitive or perhaps any motion will exacerbate the pressure on the median nerve and thus the symptoms of CTS. Static wrist splinting is the practice of applying a constant pressure to the wrist, hand, and/or arm regardless of its position or motion. U.S. Pat. No. 5,921,949, issued to Dray, discloses a device that compresses each side of the carpal tunnel and turns or twists each side to the anterior midline, using static pressure to accomplish its result.

Static splinting of the carpal joint has a number of disadvantages. First, such splints are uncomfortable which reduces patient compliance in wearing the splint. Second, by limiting the range of motion of the patient's hand, static splints limit the type of work the patient can do and interfere with the normal activities of daily living. Third, they have been shown to provide relief from the CTS symptoms for only a limited time and documented complications from extended immobilization are common.

Another approach to treating CTS has been to statically restrain pronation and/or supination with a heavy wire rather than a splint. U.S. Pat. No. 5,868,692, issued to Michniewicz, discloses such a device that restricts a user's pronation and supination to 10°, thus preventing extreme torsion that the inventor believes to aggravate those patients with prior arm and wrist injuries. Michniewicz does offer a more comfortable and less confining device than some of the other static splints, but still does not address the underlying causes of CTS.

Dynamic splinting in the traditional sense has heretofore sought to range the wrist through common planes of motion and reduce movement in some planes of motion to reduce irritation to the median nerve. Several devices are illustrative of this dynamic splinting approach. U.S. Pat. No. 5,653,680, issued to Cruz, discloses a device that dynamically controls flexion, extension, ulnar, and radial deviations with adjustable damping springs and appears to effectively limit active range of motion. The device applies rotational force to the wrist joint while pressuring to the second and third metacarpal bones, the pressure promoting a volar or dorsal transrelocation of the distal carpal row. By concentrating on the distal carpal row, Cruz places importance on independently pressuring a region removed from the carpal complex. Cruz further concentrates on the damping aspect of the invention, which is primarily directed to protect the joint against injuries due to shock than to prevent or correct a CTS condition. U.S. Pat. No. 5,413,553, issued to Downes, describes another device called a Carpal Tunnel Mitt that concentrates a mechanical opposition upon the 1st to 5th metacarpal-phalangeal region. The Carpal Tunnel Mitt is structured to deepen the carpal tunnel for decompression purposes and is distal to the actual flexion-extension mechanics occurring at the radio-carpal and mid-carpal region.

CTS and its related disorders are responsible for very high corporate overhead in terms of lost productivity, worker's compensation, and related medical costs from having to subsequently treat the condition that often becomes chronic due to the traditional paradigm of CTS diagnosis and treatment.

As can be seen, there is a need for an orthotic appliance that more precisely addresses the root causes and symptoms of CTS. There is a further need for the orthotic appliance to be inexpensive and easy to fit and use by a layperson. The appliance should be co-dynamic; that is, it should work cooperatively with the hand and carpus to achieve the therapeutic result of correcting a CTS condition. It should allow the hand and wrist to move functionally in all planes of motion so as not to interfere with the normal activities of daily living and to thereby correct the underlying causes of what becomes an inflamed condition leading to carpal tunnel compression.

SUMMARY OF THE INVENTION

In one aspect of the invention, an orthotic appliance is provided for the treatment of carpal tunnel syndrome. The appliance comprises a base means supporting a biasing means for applying a dorsally directed, self initiated, and dynamic force against a pisiform region of a carpal complex in a human hand, the biasing means conforming to a contour of the hand and supported in a conforming orientation by the base means.

In another aspect of the invention, the base means is comprised of an elastometric material such as rubber, spandex, neoprene, lycra (tm), and the like, for conforming proximity to the surface of the wrist and hand area.

In another aspect of the invention, the elastometric base means is formed as a glove for close conformance with the wrist and hand area.

These and other features, aspects and advantages of the present invention will become better understood with reference to the following drawings, description, and claims. For a better understanding of the invention, its operating advantages and the specific aspects of its uses, reference should be made to the accompanying drawings and descriptive matter in which there are illustrated preferred embodiments of the invention. The foregoing has outlined some of the more pertinent aspects of the invention. These aspects should be construed to be merely illustrative of some of the more prominent features and applications of the present invention. Many other beneficial results can be attained by applying the disclosed invention in a different manner or by modifying the invention within the scope of the disclosure. Accordingly, a better understanding of the invention will be promoted, and the detailed description of the preferred embodiments in addition to the scope of the invention will be illustrated by the accompanying drawings.

BRIEF DESCRIPTION OF THE DRAWINGS

FIG. 4 shows an ulnar view of a hand and carpus of a patient with symptoms of CTS, the proximal carpal row being translated in a volar direction;

FIG. 5 is a perspective dorsal view of a human hand and forearm showing the positioning of a first embodiment of the invention with relationship thereof;

FIG. 6 is a perspective volar view of a human hand and forearm showing the positioning of a first embodiment of the invention with relationship thereof;

FIG. 9 is a perspective side view of a human hand and forearm showing the positioning of a second embodiment of the invention with relationship thereof;

FIG. 10 presents a chart showing the amount of volar carpal translation force (VCTF) of each of a group of 26 persons organized by the severity of the CTS symptoms (mild, moderate, and severe);

FIG. 11 presents a chart showing the amount of volar carpal translation of the carpal joint of each of a group of 26 persons organized by the severity of the CTS symptoms.

DETAILED DESCRIPTION OF THE INVENTION

The following detailed description shows the best currently contemplated modes of carrying out the invention. The description is not to be taken in a limiting sense, but is made for the purpose of illustrating the general principles of the invention and the best mode for practicing the invention, since the scope of the invention is best defined by the appended claims.

Note that throughout this specification, the term "volar" shall be interpreted as "in the direction of the palm of the hand" and "dorsal" shall be interpreted as the opposite of "volar", that is, in a direction away from the palm of the hand or directed outwardly from the back of the hand. Kinematics is the science of the interplay between the dynamics and the soft tissue of a functioning joint. Unless specifically stated otherwise, all descriptions and observations shall be made from the standpoint of an individual's right hand and forearm for consistency and ease of description. The discussion that follows applies equally well to either hand or forearm.

In order to discuss the invention, it is first necessary to understand the Theory of Environmental Deformity (TED) which underlies the operation of the invention. Conventional static splinting has heretofore failed to properly address the mechanics of the carpus and hand. Conventional dynamic splinting deals with the known movements of flexion, extension, radial and ulnar deviation, i.e. movements to increase, decrease, or compress. However, the approach incorporated in the TED addresses both arthrokinematics ("kinematics of the joint") and neuromuscular changes to explain how CTS arises and to suggest a treatment for the condition. The TED identifies multiple changes in the carpal arthrokinematics that initially result from exertion of the extrinsic muscle tendon units over the flexor pulley of the wrist.

Figure 1:
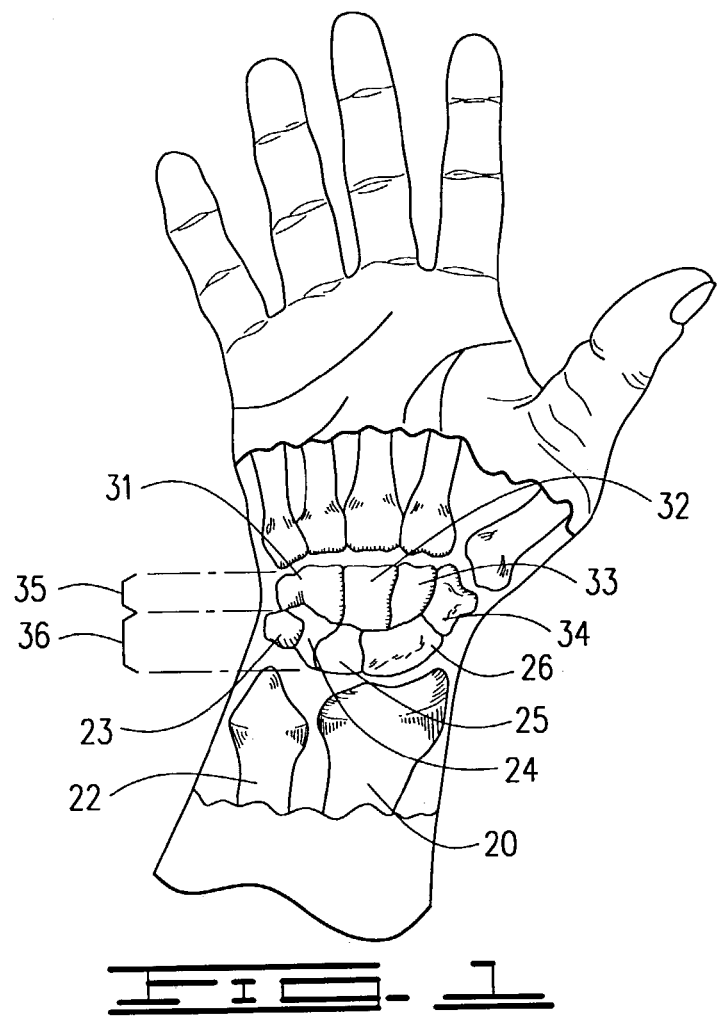
FIG. 1 shows a palmer view of a human hand with the surface removed to illustrate the relationship of the bones of the forearm, carpus, and hand.
Figure 2:
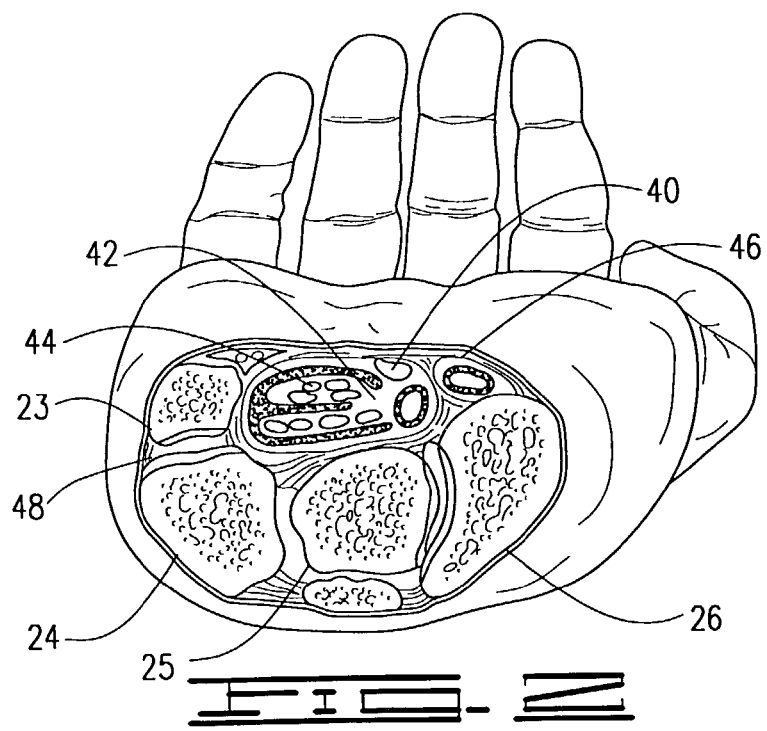
FIG. 2 shows a cross sectional view of the carpal region of a right human hand and illustrates the alignment of the proximal carpal row with relationship to the flexor retinaculum.

Referring to FIGS. 1 and 2, the carpal tunnel is a fixed cavity or area through which pass several tendons 44 and the median nerve 40. It is defined anteriorlly by the flexor retinaculum 46 and posteriorly by two sets of carpal bones. The proximal set of bones as viewed from a medial to lateral perspective is the pisiform 23, triquetrum 24, lunate 25, and scaphoid 26; this set of bones is designated as the proximal carpal row 36. The distal set of bones from a medial to lateral perspective is the hamate 31, capitate 32, trapezoidium 33, and trapezium 34; this set of bones is designated as the distal carpal row 35. The pisiform 23 is attached evenly by crucial extrinsic and intrinsic carpal structures in nine directions, where these structures include the following: piso-hamate ligament; the piso-metacarpal ligament; the proximal band of the flexor retinaculum 46; the triangular fibrocartilage complex; the flexor carpi ulnaris; the anterior portion of the medial collateral ligament; the extensor retinaculum; the abductor digiti minimi; and the pisotriquetral cartilage.

The flexor retinaculum 46 attaches to the carpus on either side of its open ends and functions as the pulley of the carpal tunnel 42 for extrinsic hand muscles to communicate between the muscle origin about the elbow and the insertion point at the fingers, thumb, and wrist. The median nerve 40 lies between the flexor retinaculum 46 and the bundles of flexor tendons 44. Functionally, the flexor retinaculum 46 adds strength to the carpus and lends efficiency to the muscle tendon action of the hand.

Figure 3:
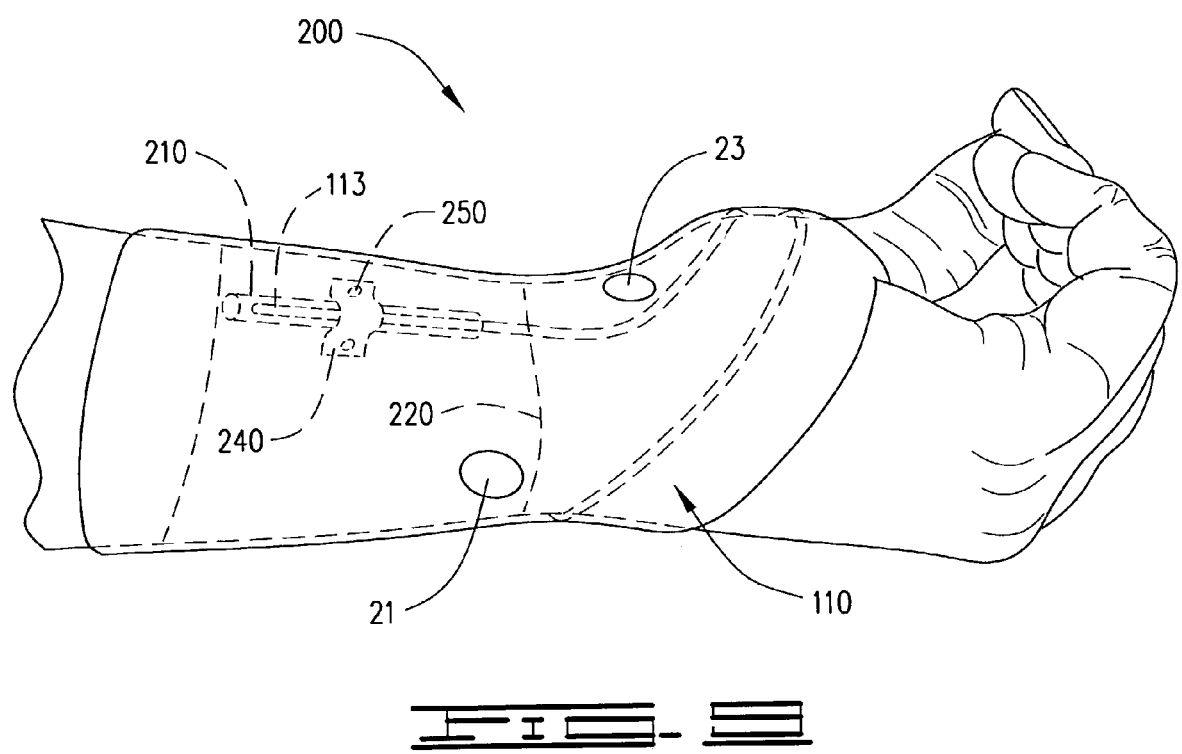
FIG. 3 shows an ulnar view of a unsymptomatic hand and carpus having a normal arrangement.
Figure 16:
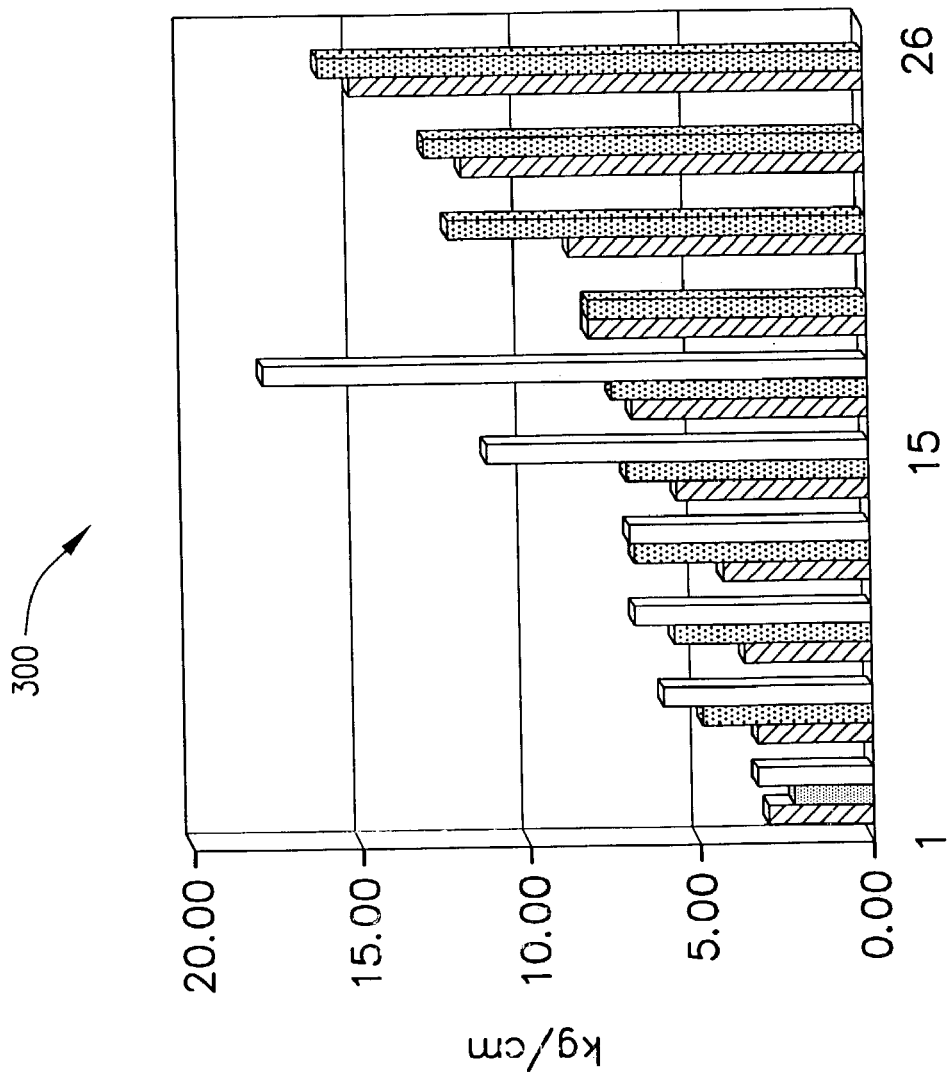

The flexor muscle tendons of the volar forearm acting on the wrist, fingers, and thumb exert a collective pulley force four times that of the extensor muscle tendons in the dorsal forearm acting to dorsally stabilize the same members of the wrist and hand. This interaction between the flexor muscles and the extensor muscles, in cooperation with the carpal ligament integrity, holds the joint in a stable position (FIG. 3) during activity. This interaction is termed "co-contraction." Co-contraction is maintained in hand and finger function and coordinated movement of the fingers and thumb until acted upon by resistance of the fingers in extension or flexion and is thereby termed contraction in the direction of resistance. The ratio flexor to extensor forces in the forearm of a normal person is typically about 4:1 ("force couple"), and it remains relatively constant during ordinary work activities throughout life.

However, some work activities tend to favor one set of muscles and tendons over the opposing set, resulting in the condition illustrated in FIG. 4. If the intensity and duration of tasks requiring finger, thumb, and wrist function favor the flexors, then the force couple increases because of hypertrophy of the flexor muscle tendon units. This hypertrophy causes a volar carpal translation (VCT) of the plane of the carpal-metacarpal complex with respect to the plane of the ulnar-radial plane, in which the planes are generally parallel; this movement is sometimes termed "volar glide". Note that this translation is not a rotation about the axis of either carpal row, but a shear movement in which the two planes are kept generally parallel. This is shown in FIG. 4 by the shear displacement of centerline 50 of the carpal-metacarpal plane in a volar direction (indicated by arrows 60) from the centerline 55 of the ulnar-radial plane.

During exertion over time, hypertrophy of flexor muscle groups alters the biomechanics of the wrist and hand, so that co-contraction gradually increases volar carpal pulley forces, thus reducing the capacity and function of the extensor muscle tendon groups from mechanical changes and neuromuscular subclinical pathology; this is referred to as proprioceptive dysfunction. The result is a greater force couple, for example, a ratio of 5:1 in favor of the more powerful over-control of the flexors. When the flexors become stronger and overly efficient, then the extrinsic extensors fail to function properly according to a well known neuromuscular process called "reciprocal inhibition"; this process is referred to as Sherington's Law in rehabilitation science. Over-control of the flexors, which occurs in contracting or co-contracting hand function, increases the force allocation over the flexor pulley (i.e. the flexor retinaculum 46), thus causing VCT in the direction indicated by arrows 60. Consequently, the long moment arm of the extensor carpi ulnaris, extensor radialis brevis, and the extensor carpi radialis longus, as well as the contribution of extensor communis, all eventually become inefficient. This inefficiency coupled with ligament length disparity results in a lack of stabilization and permissive involuntary palmer translation in the direction indicated by arrows 60 at the forearm carpal joint.

Figure 12:
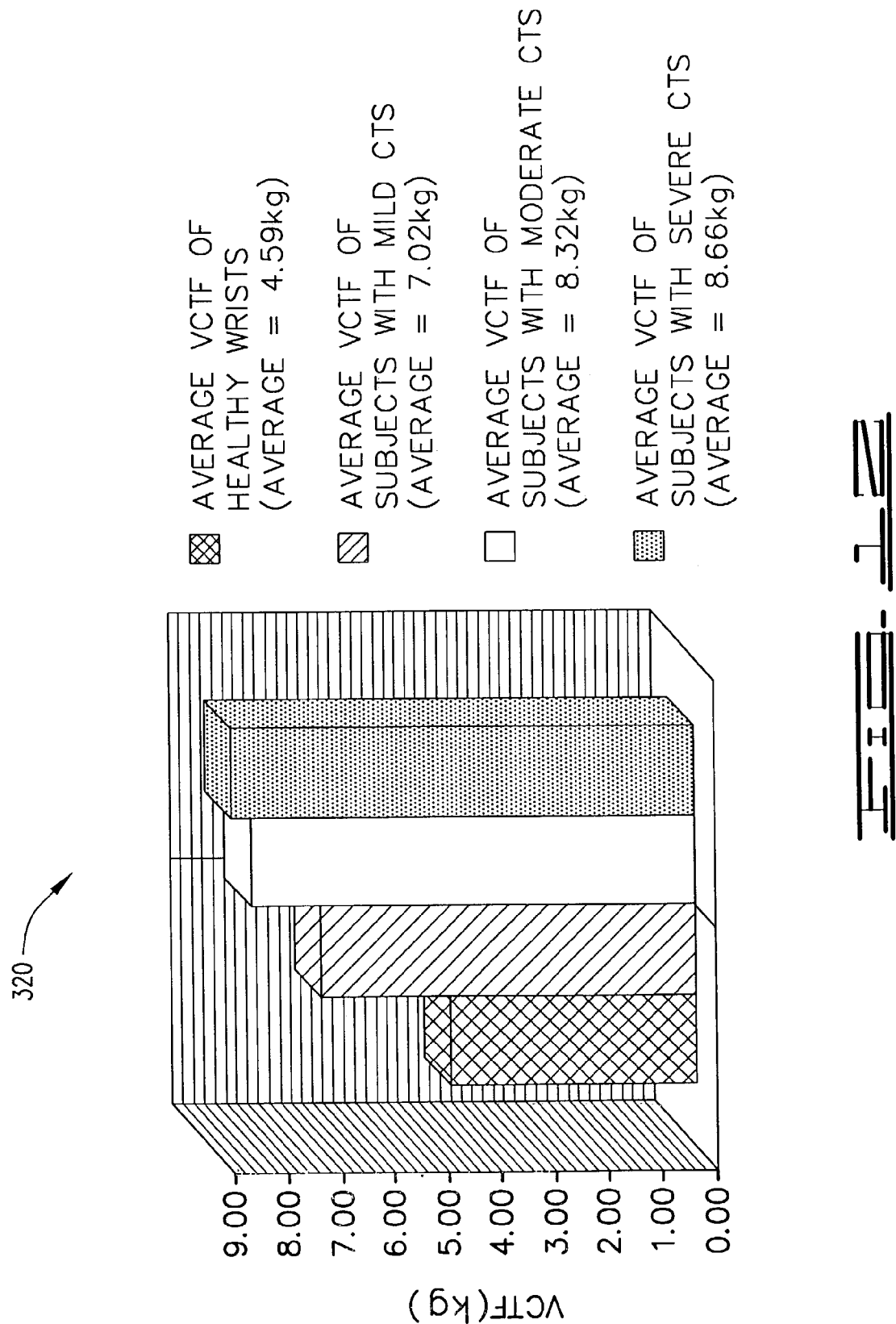
FIG. 12 presents a chart showing a summary of the averages for VCTF for each of the three groups and a control group.

A test was performed using 26 patients sent by referring physicians for treatment. Each patient had been classified has having mild, moderate, or severe CTS according to the results of electromyography. The VCT and the force causing the VCT (i.e. volar carpal translation force, or VCTF) were measured for each patient. The VCT and VCTF for a control group of asymptomatic individuals were also measured. The results of the testing were averaged and graphed according to the graphs in FIGS. 10, 11, and 12. Graph 300 shows the raw numbers of VCTF measured in kg/cm for each of the 26 individuals and ordered within each of the three classes of CTS severity. Graph 310 shows the raw numbers of VCT measured in centimeters for each of the 26 patients, again ordered within each of the three classes of CTS severity. These graphs 300, 310 show a marked positive correlation between the increasing degree of severity in CTS symptoms and the increasing amount of VCT and VCTF measured in those individuals. Graph 320 summarizes the averages of each of these groups and compares them with the average VCTF of the control group. In each case of CTS, the VCTF was higher than that of an asymptomatic person.

The flexor retinaculum 46 is the carpal ligament that spans the carpal canal and is the primary pulley for contraction and co-contraction activities of the hand. This ligament is severed during invasive surgical intervention to relieve the pain and paresthesia of CTS. By its location and nature, the flexor retinaculum 46 serves as the pulley of all extrinsic motor activities of the hand. Pulley force increases due to force couple changes are therefore concentrated at the flexor retinaculum 46 and must promote anterior translation and distributed force over the attachments of the carpus, thus encouraging an anterior medial stress on the carpal bodies.

The effect of the volar translating flexor forces, acting upon the flexor retinaculum 46 as a pulley, attenuate the flexor retinaculum 46 and residual force distribution conveys forces anteriorlly and medially. This places traction forces to the ligament ends of the carpus. Each night, while the muscles are at rest, the volar intracarpal ligament segments restore their normal position grossly; however, some minute anteriomedial deformity remains, and slack of the flexor retinaculum 46 is concurrently taken up by contractile forces of this and the other ligaments. Numerous cycles of force followed by rest develop an established deformation that is manifested by narrowing the horseshoe ends of the carpal tunnel. The horseshoe ends are held in position by a clinically recognized, thickening flexor retinaculum 46 and other volar carpal ligaments, resulting in a transverse deformity. Simultaneously, the flexor retinaculum 46 acting as a pulley is subjected to the load produced by the finger and thumb function so that a volar glide is initiated. This volar glide of the carpal metacarpal complex attenuates the predisposed thin dorsal carpal ligaments originating from the distal radial ulna. Since the volar carpal ligaments (including the flexor retinaculum 46) collectively become less stressed, they begin to contract (shorten), thus encouraging the anteriomedial collapse (diminished carpal volume) of the intercarpal spaces simultaneous to a longitudinal deformity (or VCT).

The long moment arm of the carpal muscle tendon units are only capable of stabilization of the carpus when the muscle tone is within normal limits, i.e. flexor to extensor force ratio of approximately 4:1. These forces acting on the carpus in flexion are convergent toward the muscle origin and are regulated by interplay of antagonists, pulleys, and joint alignment. A variation of one or more serves to simplify convergence towards a direct line to this point of origin and shorten the distance therebetween. This resulting force decreases the biomechanical advantage, manifested by a volar shift of the axis of the proximal carpal row 36 in a shear movement. This accounts for the propensity of patients with CTS to develop odd compensatory behaviors like flexing the wrist during power grasping to exert maximum power, conceivably to account for the change in position of the more volarly placed flexor retinaculum. Volume of the carpal tunnel 42 is further reduced and any other abnormal predisposition will hasten onset of the condition. Thus, the resistance that the flexor retinaculum 46 and related volar ligaments encounter when returning the carpal metacarpal complex to a neutral position, i.e. dorsal glide, is indicative of the severity of the condition of CTS or the propensity of the subject to incur the condition.

Carpal stabilization is essential to restore normal carpus and hand function in CTS patients. Stabilization is believed to depend largely upon neuromuscular and proprioceptive control, a concept that is absent from other conservative methods of managing CTS. Stabilization consists of restoring the normal ligament length and integrity and restoring the normal force couple. Though static splinting has been employed to relieve CTS symptoms, such relief is only temporary. Static splinting positions the carpus so that the flexors and extensors may properly apply their forces to the carpal area, but the fundamental imbalance of forces remains; muscles atrophy, range of motion is lost, and no lasting clinical benefit has been determined when splints are removed. Flexor over-control reestablishes the condition. Static splinting thus does not permanently restore proprioceptive control and normal arthrokinematics, and it can only provide temporary relief of symptoms. The static management of CTS thus impairs proprioceptive control and results in further dysfunctional arthrokinematic conditions maintained by abnormal force couple.

In addressing carpal stabilization, the TED identifies a bone of major importance in the proximal carpal row 36, i.e. the pisiform 23. As previously discussed, the pisiform 23 functions as the attachment point for support structures in nine directions; these structures include in particular the piso-hamate ligament, the piso-metacarpal ligament, the proximal band of the flexor retinaculum, the triangular fibrocartilage complex, the flexor carpi ulnaris, the anterior portion of the medial collateral ligament, the extensor retinaculum, the abductor digiti minimi, and the pisotriquetral cartilage. As flexor retinaculum 46 and volar intra-carpal ligaments undergo changes associated with CTS, the VCT increases, leaving the pisiform 23 susceptible to deformation by altered periarticular attachments thereto. In cases where CTS is severe, the pisiform 23 often succumbs to osteoarthritis and becomes immobilized. When the pisiform 23 is immobilized, the piso-triquetral joint 48 (the joint between the pisiform 23 and the triquetrum 24 in the proximal carpal row 36) is unable to produce proximal excursion during co-contraction and distal excursion during composite flexion at resistance.

The TED identifies at least three different types of dysfunction due to VCT affecting the moment arm of the pisiform 23. These types are based on the classification of the nine pisiform 23 attachments as being either distal pisiform attachments or proximal pisiform 23 attachments. They are documented in the abstract paper presentation to the American Society for Peripheral Nerve, entitled "Pisiform Arthrokinematics and Carpal Tunnel Syndrome," by G. R. Williams, p. 645 Vol. 18, No. 7., October 2002, *Journal of Reconstructive Microsurgery*, which is included herein in its entirety by reference. In summary, Type I pisiform behavior is caused by excessive grasping of the hand to produce contraction of the distal pisiform attachments. Type II pisiform behavior is caused by excessive co-contracting of the hand to produce contraction the proximal pisiform attachments. Type III pisiform behavior is caused by a combination of excessive contracting and co-contracting activities to produce multi-planar immobilization of the pisiform. A lack of pisiform mobility due to Type I or Type II displacement or Type III immobilization is intrinsically linked to intracarpal pulley forces translating the wrist in a volar glide.

The TED focuses generally upon volar glide and specifically on the limited excursion of the piso-triquetral joint 48 as a major symptom of CTS changes in arthrokinematics; the TED thus proposes a treatment to dynamically encourage realignment of the carpus, mobilization of the pisiform, and mobilization and stabilization of the carpal joint. To do this, the TED identifies a plane of motion critical to treating CTS called dorsal glide. Dorsal glide, the opposite of volar glide, is the dorsal movement of the plane of the carpal metacarpal complex in a shear movement keeping it parallel with the plane formed by the forearm, radius, and ulna; such movement occurs primarily at the proximal carpal row 36. According to the TED, a continuous encouragement of dorsal glide will reestablish normal carpal height while maintaining and promoting normal range of movement in all other planes of motion involved in the standard activities of daily living. The preferred location to apply force encouraging dorsal glide is generally in the region of the pisiform 23 leveraging the proximal carpal row 36. Through an interactive, dynamic, resistance-oriented application of dorsal glide force at the pisiform 23 and pisiform region, the TED addresses both movement (kinematics) and control (neuromuscular) aspects treating CTS. Previous solutions have concentrated upon the flexion/extension, ulnar/radial deviation, and supination/pronation ranges of motion (i.e. rotational) but have neglected the valuable contribution of dorsal and volar glide (i.e. translational) involved in and critical to the normal arthrokinematics of carpal and hand function.

The TED suggests a practical approach to the treatment of CTS. Thus, according to this theory, an invention is provided that interactively provides a dynamic force directly to the pisiform region in order to encourage dorsal glide in a human hand. An interactive, dynamic orthotic appliance embodying the invention is disclosed that provides dynamic resistance against volar glide (excessive in CTS patients) of the proximal carpal row 36 and thus promotes dorsal glide throughout the normal range of motion of a human hand during normal activities of daily living. The orthotic appliance may utilize a biasing means to communicate a dorsally directed force against a point of leverage to dorsally translate the carpal-metacarpal complex in a shear movement. A preferred point of leverage identified by the TED is in the region of the pisiform 23, i.e. the general area of the hand that is either directly on the pisiform 23 or somewhat distal to the pisiform along the ulnar side of the palm. The goal is to minimize or eliminate any interference with normal hand and wrist motion while applying an as-needed, self-initiated counter force opposing VCT to the pisiform region of the hand in order to achieve a dorsal realignment of the carpus with respect to the forearm, i.e. to promote dorsal glide, and to maintain that alignment by eccentric input of the weaker extensor muscle tendon groups. Dorsally directed force of as little as two pounds applied to the pisiform region while the hand is engaged in multiplanar unrestricted use has been shown to eliminates symptoms typically within 24 hours.

In a first embodiment 100 of the invention, shown in FIGS. 5 and 6, a biasing means is provided to urge the proximal carpal row 36 in a dorsal direction. The preferred form of the biasing means is a resilient wire 110 formed as an elongated "U", the wire having a loop 111, a first end 112, and a second end 113. The resilient wire 110 may be structured to supply a counter force of approximately 2 pounds during co-contraction activity of the fingers and thumb with the carpus in a neutral position. It may also provide up to 8 pounds of resistive force between 0° (no flexion) and 90° (full flexion) of carpus and hand. The loop 111 of resilient wire 110 is positioned generally at the pisiform region 27, while the two ends 112, 113 of the resilient Wire are conformingly wrapped about the hand and carpus to eventually rest at a generally diagonal position on the dorsum 120 of the forearm. Portions 114, 115 of the resilient wire near ends 112, 113 may be preferably positioned on either side of the ulnar styloid 21. Each of the two ends 112, 113 may be bent into a circular or spiral form so that the sharp ends of the resilient wire 110 do not snag the enclosing base means and may slide freely within the sheath of the enclosing base means. The ends 112, 113 may be kept aligned and in place by including pockets 116, 117 for insertion therein, so that the pockets 116, 117 guide the longitudinal movement of the respective ends 112, 113.

The first end 112 and the second end 113 may be either allowed to freely move in a generally longitudinal manner along the dorsum 120 of the forearm or else constrained from movement relative to the dorsum 120; such constraint may be achieved by intuitive means such as stitching the end to the base means. By permitting movement of the first end 112, the second end 113, or both ends 112, 113, or by restraining both ends 112, 113, varying degrees of control of the loading of the biasing means may be accomplished. Also, allowing movement of the ends 112, 113 accommodates the observed lengthening of the wrist in flexion and shortening of the wrist in extension and allows the biasing means to track hand and wrist movement more closely. In a first such configuration, if both ends 112, 113 are fixed in place, then this correlates to the control provided by a conventional static splint. If in a second configuration both the first end 112 and second end 113 may move within the first pocket 116 and second pocket 117, respectively, either or both of the ends 112, 113 may then be engaged for research purposes with sensors, controlled motor units, or any other means to move or to detect position and resistance.

The resilient wire 110 is kept in conforming relationship with the hand, wrist, and forearm by a base means, preferably a glove 130 comprised of an elastometric material such as rubber, spandex, neoprene, lycra (a registered trademark of E. I. du Pont de Nemours and Company, Wilmington, Del.) or other similar materials or fabrics possessing analogous properties of stretchability and/or flexibility. The resilient wire 110 may be stitched into the lining of glove 130 to allow glove 130 to maintain the conforming relationship with the hand, wrist, and forearm. Fabric reinforcements (not shown) may be added at various points along resilient wire 130 to ensure that it is kept close to the skin of the hand, wrist, or forearm during their normal range of motion.

Figure 7:
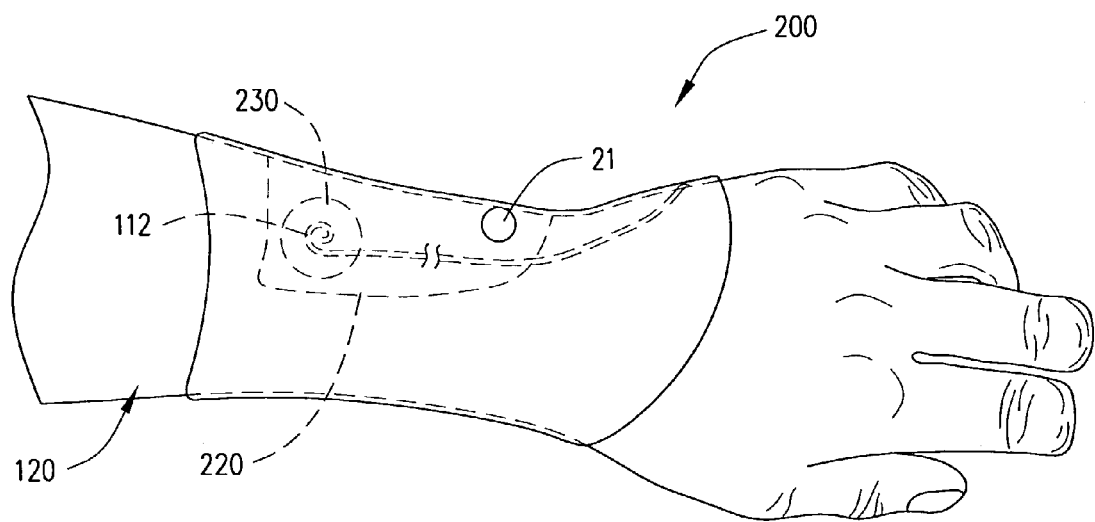
FIG. 7 is a perspective dorsal view of a human hand and forearm showing the positioning of a second embodiment of the invention with relationship thereof.
Figure 8:
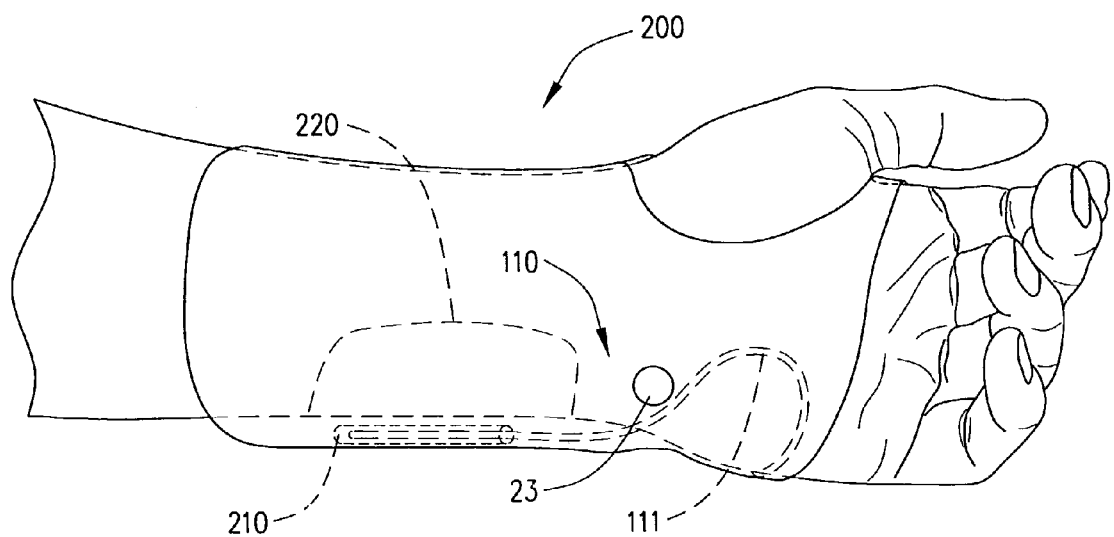
FIG. 8 is a perspective volar view of a human hand and forearm showing the positioning of a second embodiment of the invention with relationship thereof.

A second embodiment 200 of the invention is shown in FIGS. 7, 8, and 9, to illustrate varying ways in which the ends 112, 113 can be positioned along the forearm and wrist and in which they may be secured with relationship to the forearm and wrist. A plate 220 is affixed to the fabric of the base means to facilitate alignment with the forearm and wrist. It may be constructed of any suitable rigid material, but preferably it may be fabricated of a material known as dead soft aluminum to those skilled in the art. Plate 220 may have an indentation into which the ulnar styloid 21 may be placed. The first end 112 may be arbitrarily positioned by the plate 220 along the dorsum 120 of the forearm and fixedly held in place to prevent subsequent movement by a patch 230 comprised of a standard hook and loop structure. The second end 113 of the resilient wire 110 may be aligned along the ulna 22 of the forearm and may be loosely enclosed within a tube 210. Tube 210 may be comprised of any suitable material that is rigid and allows unobstructed longitudinal passage of the end 113. It may be preferably constructed of Teflon (tm). The term "Teflon" is a registered trademark of E. I. du Pont de Nemours and Company, Wilmington, Del. Tube 210 may be secured in alignment with ulna 22 by stitching or, as shown, by a metal strap 240 attached to plate 220 by rivets 250. Although rivets are shown, any standard connection means well known to those skilled in the art may be used, e.g. by screws, rivets, welding, braising, and adhesives.

As has been demonstrated the present invention provides an advantageous appliance and technique for prevention and correction of carpal tunnel syndrome within a human carpal joint. While the preferred embodiments of the present invention have been described, additional variations and modifications in those embodiments may occur to those skilled in the art once they learn of the basic inventive concepts. Therefore, it is intended that the appended claims shall be construed to include both the preferred embodiment and all such variations and modifications as fall within the spirit and scope of the invention.

I claim:

1. An orthotic appliance for the treatment of carpal tunnel syndrome in a carpus between a hand and a forearm of a human, the carpus being aligned to a carpus plane, the forearm being aligned to a ulnar-radial plane, the appliance comprising a biasing means consisting substantially of a resilient wire formed into an elongated U shape with two substantially parallel wire portions adapted for positioning on two sides of an ulnar styloid bone and a loop formed therebetween in comforming relationship to a surface of the forearm and the hand, the resilient wire having a first end adapted for positioning generally on a dorsum of the forearm and adjacent the ulnar bone and a second end positioned generally adjacent to the first end and adapted for positioning on the dorsum of the forearm, the loop adapted to be positioned on the volar surface of the hand in the region of the pisiform bone, wherein the loop of the resilient wire is arranged to provide a dynamic, dorsally directed force in the general region of a pisiform bone in the carpus when the carpus is in a neutral position, the dynamic, dorsally directed force arranged to promote dorsal glide against a proximal carpal row of the carpus by leveraging against the forearm; and a base means maintaining the biasing means in conforming relationship with the surface of the hand and forearm, wherein the base and biasing means cooperatively allow movement of the hand, carpus, and forearm during extension and flexion of the hand, during pronation and supination of the forearm and carpus, and during ulnar and radial deviation of the hand without preventing the normal activities of daily living.

2. The appliance described in claim 1, wherein the base means is constructed of an elastometric material.

3. The appliance described in claim 2, wherein the elastometric material is chosen from the group consisting of rubber, lycra, spandex, and neoprene.

4. The appliance described in claim 1, wherein the base means is a glove.

5. The appliance in claim 1, wherein the first end is adapted for positioning generally along the ulnar side of the forearm and allowed to move proximally and distally along the forearm during movement of the hand and carpus, the second end adapted for fixed positioning on the dorsum of the forearm, wherein the second end is constrained from movement.

6. The appliance in claim 1, wherein the second end is adapted for proximal and distal movement along the dorsum of the forearm, the first end adapted for fixed positioning along the ulnar side of the forearm, wherein the first end is constrained from movement.

7. The appliance in claim 1, wherein the first end is adapted for fixed positioning along the ulnar side of the forearm, the second end adapted for fixed positioning on the dorsum of the forearm, wherein both the first end and the second end are constrained from movement.

8. The appliance in claim 1, wherein the distal portions of the first and second ends of the wire are adapted for positioning on opposite sides of an ulnar styloid of the forearm.

9. The appliance in claim 1, wherein the dorsally directed force is at least two pounds during co-contraction of the fingers and thumb when the carpus is in a neutral position.

10. The appliance in claim 1, wherein the dorsally directed force increases to about 8 pounds when the hand and carpus are moved towards 90° in flexion.

11. An orthotic appliance for co-dynamic treatment of carpal tunnel syndrome exhibited by a human carpus, the carpus associated with a forearm and a hand, the orthotic appliance comprising
   a resilient wire consisting substantially of a bent elongate U shaped wire with two substantially parallel wire portions adapted for positioning on two sides of an ulnar styloid bone and forming a loop adapted for positioning on the volar surface of the hand in the region of the pisiform bone of the carpus in order to apply a dorsally directed force on the hand; the resilient wire having a first end adapted for positioning on the dorsum of the forearm and adjacent to an ulnar bone and a second end positioned adjacent to the first end and adapted for positioning on the dorsum of the forearm, the resilient wire adapted to conform to the surface of the hand, carpus, and forearm; and
   a base means adapted for maintaining the resilient wire in conforming relation with a surface of the hand, carpus, and forearm;
   wherein the resilient wire and base means cooperatively promote dorsal glide of the proximal carpal row of the carpus while allowing volitional motion in any plane, thereby allowing the human to perform standard activities of daily living.

12. The appliance described in claim 11, wherein
   the first end is adapted for proximal and distal longitudinal movement along the ulna as the hand extends and flexes, as the forearm and wrist pronate and supinate, and as the hand deviates ulnarly and radially; and
   the second end is fixedly adjustable on a portion of the base means adapted to cover the dorsum of the forearm and thereby constrained from the proximal and distal longitudinal movement.

13. The appliance described in claim 11, wherein
   the second end is allowed to move proximally and distally along the dorsum as the hand and carpus extend and flex, as the forearm and wrist pronate and supinate, and as the hand deviates ulnarly and radially; and
   the first end is fixed on a portion of the base means covering the ulnar aspect of the forearm and thereby constrained from the proximal and distal longitudinal movement.

14. The appliance described in claim 11, wherein the base means further comprises
   a plate curved to accommodate the ulnar side of the forearm;
   a tube fixedly attached to the plate and adapted for longitudinal alignment with the ulna of the forearm, the tube receiving the first end of the wire for sliding movement therein during motion of the hand and carpus.

15. A method for the co-dynamic treatment of carpal tunnel syndrome exhibited by a human carpus, the carpus associated with a forearm and a hand having fingers and a thumb, the method comprising the steps of
   forming a resilient wire comprising a first end, a second end, and a loop, the resilient wire conforming to a surface of the carpus, hand, and forearm; providing a base means for maintaining the resilient wire in conforming relationship with the surface of the hand and the forearm;
   aligning the first end on the dorsum of the forearm and along an ulna of the forearm for proximal and distal longitudinal movement along the ulna during extension and flexion of the hand, during pronation and supination of the forearm and carpus, and during ulnar and radial deviation of the hand;
   aligning the second end on and along the dorsum of the forearm;
   aligning the loop in a region of a pisiform bone of the carpus and on the volar surface of the hand;
   constraining a selected end from proximal and distal movement along the forearm while allowing the remaining end to move proximally and distally along the forearm, wherein the selected end is selected from a group consisting of the first end and the second end; and
   maintaining the resilient wire in conformance with the surface during extension and flexion of the hand, during pronation and supination of the forearm and carpus, and during ulnar and radial deviation of the hand;
   wherein the resilient wire promotes dorsal glide of the proximal carpal row of the carpus during flexion activities of the fingers and thumb and of the middle carpal row during extension activities of the fingers and thumb without obstructing motion in any plane, thereby allowing the human to perform standard activities of daily living.

16. The method of claim 15, wherein the resilient wire supplies a counter force of at least about two pounds during co-contraction activity of the fingers and thumb while the carpus is in a neutral position.

17. The method of claim 15, wherein the resilient wire supplies a counter force of up to approximately eight pounds of resistive force when the hand and carpus are moved towards 90° in flexion.

18. The method of claim 15, wherein the selected end is the second end.

19. The method of claim 15, wherein said base means is a glove.

20. The method of claim 15, wherein the selected end is the first end.

* * * * *